(12) United States Patent
Shibata et al.

(10) Patent No.: US 7,749,497 B2
(45) Date of Patent: Jul. 6, 2010

(54) USE OF ADSORBENT CARBON MICROSPHERES FOR THE TREATMENT OF IRRITABLE BOWEL SYNDROME

(75) Inventors: Akiko Shibata, San Diego, CA (US); Laurent Fischer, Del Mar, CA (US)

(73) Assignee: Ocera Therapeutics, Inc., San Diego, CA (US)

( * ) Notice: Subject to any disclaimer, the term of this patent is extended or adjusted under 35 U.S.C. 154(b) by 181 days.

(21) Appl. No.: 11/567,093

(22) Filed: Dec. 5, 2006

(65) Prior Publication Data

US 2007/0141045 A1 Jun. 21, 2007

Related U.S. Application Data

(60) Provisional application No. 60/748,065, filed on Dec. 6, 2005.

(51) Int. Cl.
*A61K 33/44* (2006.01)
(52) U.S. Cl. .................................. 424/125; 424/400
(58) Field of Classification Search ..................... None
See application file for complete search history.

(56) References Cited

U.S. PATENT DOCUMENTS

| | | | |
|---|---|---|---|
| 3,642,986 A | 2/1972 | Welch et al. | |
| 4,162,306 A | 7/1979 | Laves | |
| 4,761,284 A | 8/1988 | Nishimura | |
| 4,822,765 A | 4/1989 | Nishimura | |
| 5,554,370 A | 9/1996 | Uehara et al. | |
| 6,165,482 A | 12/2000 | Grimberg | |
| 6,830,753 B2 * | 12/2004 | Sonobe et al. | 424/400 |
| 2003/0118581 A1 | 6/2003 | Sonobe et al. | |

FOREIGN PATENT DOCUMENTS

| | | |
|---|---|---|
| EP | 0688566 A1 | 12/1995 |
| EP | 0958833 A1 | 11/1999 |
| RU | 2057533 | 4/1996 |
| WO | WO 2007/067663 A | 6/2007 |

OTHER PUBLICATIONS

Araki et al., Shoka to Kyushu (1997), 20(2), 25-30 (Abstract).*
www.helpforibs.com/footer/rome_guidelines.asp.*
Anderson, et al. W1300 AST-120: A Novel, Engineered Carbon Microsphere Product for Use in Chronic Inflammatory Bowel Disease and Liver Dysfunction, Apr. 1, 2008, p. A-675, vol. 134, No. 4, Gastroenterology, Elsevier, Philadelphia, Pennsylvania.
Baidoo, et al., M1975: Rifaximin is an Effective Antibiotic for the Treatment of Pouchitis, Gastroenterology, Apr. 1, 2005, p. A-797, vol. 128, No. 4 Suppl 2, Elsevier, Philadelphia, Pennsylvania.
Friedman, G., Treatment of the Irritable Bowel Syndrome, Gastroenterol Clin North Am., Jun. 1991, p. 325-333, 20 (2) (Abstract only).
Gardiner, et al., Adsorbents as Antiendotoxin Agents in Experimental Colitis, Gut, 1993, p. 51-55, 34.
Gionchetti, et al., Review Article: Treatment of Mild to Moderate Ulcerative Colitis and Pouchitis, Alimentary Pharmacology & Therapeutics, Jul. 1, 2002, p. 13-19 vol. 16, No. Suppl. 4, Blackwell Scientific Publications, Ltd., Cambridge, Great Britain.
Hübner, et al., Charcoal Tablets in the Treatment of Patients With Irritable Bowel Syndrome, Advances in Therapy, Sep./Oct. 2002, p. 245-252, vol. 19, No. 5.
Jain, et al., Efficacy of Activated Charcoal in Reducing Intestinal Gas: A Double-Blind Clinical Trial, Am J Gastroenterol, Jul. 1986, p. 532-535, 81(7) (Abstract only).
Mohanty, et al., W1412: Management of Pouchitis of the Ileoanal Pouch with Inflixirnab, Apr. 1, 2004, p. A-631, vol. 126, No. 4, Suppl. 2, Elsevier, Philadelphia, Pennsylvania.
EPO Examination Report, Application No. 06 839 125.9-2112 (OCERA.006VEP), mailed Feb. 11, 2009.
PCT International Search Report and Written Opinion, International Application No. PCT/US2006/046623 (OCERA.006VPC), mailed Apr. 23, 2007.
PCT Written Opinion, International Application No. PCT/US2006/046623 (OCERA.006VPC), mailed Mar. 7, 2008.
Di Stefano, et al., Non-Absorbable Antibiotics for Managing Intestinal Gas Production and Gas-Related Symptoms, Aliment Pharmacol Ther, 2000, p. 1001-1008, vol. 14, Blackwell Science Ltd.
Lembo, et al., "Effect of Alosetron on Bowel Urgency and Global Symptoms in Women With Sever, Diarrhea-Predominant Irritable Bowel Syndrome: Analysis of Two Controlled Trials", Clinical Gastroenterology and Hepatology, 2004, p. 675-682, vol. 2, No. 8, American Gastroenterological Association.
Leventer, et al., Clinical Trial: Dextofisopam in the Treatment of Patients With Diarrhoea-Predominant or Alternating Irritable Bowel Syndrome, Alimentary Pharmacology & Therapeutics, 2008, p. 197-206, vol. 27, Pharmos Corp.
Muller-Lissner, et al., Tegaserod is Effective in the Initial and Retreatment of Irritable Bowel Syndrome With Constipation, Aliment Pharmacol Ther, 2005, p. 11-20, vol. 21, Blackwell Publishing Ltd.
Nikolaev, V. G.et al., Detoxification Sorption Method in Clinic, $1^{st}$ Belarusian Republican Conference, 1983, Minsk, (in Russian), "Concise explanation provided in cover letter."

* cited by examiner

*Primary Examiner*—Phyllis G. Spivack
(74) *Attorney, Agent, or Firm*—Knobbe, Martens, Olson & Bear, LLP

(57) ABSTRACT

Adsorbent carbon microspheres are administered to treat irritable bowel syndrome or symptoms associated with irritable bowel syndrome.

19 Claims, 1 Drawing Sheet

USE OF ADSORBENT CARBON MICROSPHERES FOR THE TREATMENT OF IRRITABLE BOWEL SYNDROME

CROSS-REFERENCE TO RELATED APPLICATIONS

This application claims the benefit of U.S. Provisional Application No. 60/748,065, filed Dec. 6, 2005, which is incorporated herein by reference in its entirety.

BACKGROUND OF THE INVENTION

1. Field of the Invention

One aspect of the present invention relates to the treatment of irritable bowel syndrome and symptoms associated with irritable bowel syndrome using adsorbent carbon microspheres.

2. Description of the Related Art

Irritable bowel syndrome (IBS) is a gastrointestinal disorder characterized by altered bowel habits without the presence of detectable structural abnormalities. IBS is fairly common and makes up 20-50% of visits to gastroenterologists. Diagnosis of IBS is based on clinical presentation. Patients with IBS fall into two broad clinical groups. Most commonly, patients have abdominal pain associated with altered bowel habits that consist of constipation, diarrhea, or both. The second group consists of patients with painless diarrhea. Some practitioners apply the Rome II criteria for the diagnosis of IBS. This criteria requires at least 12 weeks, which need not be consecutive, in the preceding 12 months of abdominal discomfort or pain that has at least two of the following three features: 1) relieved by defecation, 2) onset associated with changes in stool frequency, or 3) onset associated with changes in stool form. Recently, the Rome II criteria has been updated by the promulgation of the Rome III criteria, which requires recurrent abdominal pain or discomfort at least 3 days per month in a 3 month period where the pain or discomfort has at least two of the three following features: 1) improvement with defecation, 2) onset associated with changes in stool frequency, or 3) onset associated with changes in stool form. Patients with IBS also frequently complain of abdominal distention and increased belching or flatulence. In some cases, IBS is diagnosed by identification of positive clinical features along with elimination of possible organic diseases.

SUMMARY OF THE INVENTION

One embodiment disclosed herein includes a method of treating one or more symptoms of irritable bowel syndrome, comprising identifying a subject suffering from irritable bowel syndrome and administering to the subject adsorbent carbon microspheres having a particle size of about 0.01 to about 2 mm. In one embodiment, the irritable bowel syndrome is characterized by abdominal discomfort or pain and one or both of constipation and diarrhea. In one embodiment, the irritable bowel syndrome is characterized by abdominal discomfort or pain that has at least two characteristics selected from the group consisting of: 1) the discomfort or pain is relieved or improved by defecation, 2) onset of the discomfort or pain is associated with changes in stool frequency, and 3) onset of the discomfort or pain is associated with changes in stool form. In one embodiment, the irritable bowel syndrome is characterized by diarrhea without abdominal pain or constipation. In one embodiment, the irritable bowel syndrome comprises loose or watery stools in at least about 25% or greater of bowel movements. In one embodiment, the irritable bowel syndrome satisfies Rome II criteria. In one embodiment, the irritable bowel syndrome satisfies Rome III criteria. In one embodiment, an amount of the adsorbent carbon microspheres sufficient to achieve at least about a 50% reduction in the number of days the subject experiences abdominal pain is administered. In one embodiment, about 2 g of adsorbent carbon microspheres are administered three times daily.

Another embodiment disclosed herein includes a method of treating irritable bowel syndrome, comprising identifying a subject suffering from abdominal discomfort or pain associated with irritable bowel syndrome and administering to the subject an amount of adsorbent carbon microspheres having a particle size of about 0.01 to about 2 mm sufficient to reduce the abdominal discomfort or pain. In one embodiment, the amount of the adsorbent carbon microspheres is sufficient to achieve at least about a 50% reduction in the number of days the subject experiences abdominal pain or discomfort.

Another embodiment disclosed herein includes a method of treating irritable bowel syndrome, comprising identifying a subject suffering from abdominal distention, increased belching, or flatulence associated with irritable bowel syndrome and administering to the subject an amount of adsorbent carbon microspheres having a particle size of about 0.01 to about 2 mm sufficient to reduce gas in the subject.

In some of the above embodiments, the adsorbent carbon microspheres have a particle size of about 0.02 to about 1 mm. In some of the above embodiments, the adsorbent carbon microspheres have a particle size of about 0.05 to about 0.8 mm. In some of the above embodiments, the adsorbent carbon microspheres have a specific surface area of about 700 $m^2/g$ or more as determined by a BET method. In some of the above embodiments, the adsorbent carbon microspheres have a specific surface area of about 700 $m^2/g$ to about 2500 $m^2/g$ as determined by a BET method. In some of the above embodiments, the volume of pores in the adsorbent carbon microspheres having a pore diameter of about 20 to about 15,000 nm is from about 0.04 mL/g to about 0.10 mL/g. In some of the above embodiments, the total amount of acidic groups in the adsorbent carbon microspheres is from about 0.30 to about 1.20 meq/g. In some of the above embodiments, the total amount of basic groups in the adsorbent carbon microspheres is from about 0.20 to about 1.00 meq/g.

DETAILED DESCRIPTION OF CERTAIN EMBODIMENTS

Figure 1:
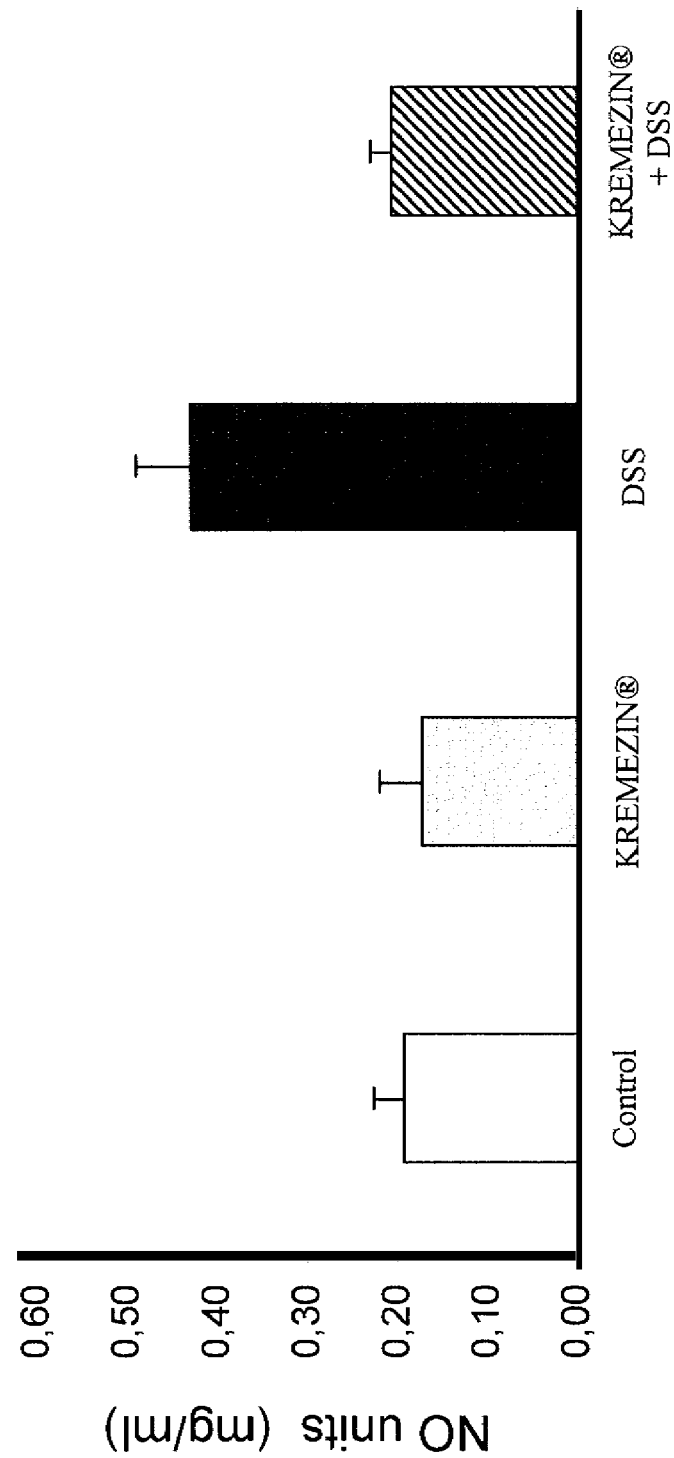
FIG. 1 is a bar graph depicting serum nitric oxide levels in mouse models having DSS-induced colitis.

In some embodiments, IBS or symptoms associated with IBS are treated by administering adsorbent carbon microspheres to a patient. In some embodiments, the particle size of the microspherical carbon is from about 0.01 to about 2 mm in diameter. In some embodiments, the diameter is from about 0.02 to about 1 mm. In still other embodiments, the diameter is from about 0.05 to about 0.8 mm. In some embodiments, the adsorbent carbon microspheres have a specific surface area of about 700 $m^2/g$ or more, such as determined by a BET method. In some embodiments, the specific surface area is from about 700 $m^2/g$ to about 2500 $m^2/g$. In some embodiments, the volume of pores in the carbon particles having a pore diameter of about 20 to about 15,000 nm is from about 0.04 mL/g to about 0.10 mL/g. In some embodiments, the total amount of acidic groups on the carbon is from about 0.30 to about 1.20 meq/g. In some embodiments, the total amount of basic groups on the carbon is from about 0.20 to about 1.00 meq/g. Suitable forms of adsorbent carbon microspheres are also described in U.S. Pat. Nos. 4,681,764 and 6,830,753 and U.S. Application Publication Nos. 2005/0112114; 2005/0079167; and 2005/0152890; all of which are incorporated herein by reference in their entirety.

In some embodiments, the irritable bowel syndrome treated is characterized by abdominal discomfort or pain and one or both of constipation and diarrhea. In some embodiments, the irritable bowel syndrome treated is characterized by abdominal discomfort or pain that has at least two characteristics selected from the group consisting of: 1) the discomfort or pain is relieved or improved by defecation, 2) onset of the discomfort or pain is associated with changes in stool frequency, and 3) onset of the discomfort or pain is associated with changes in stool form. In some embodiments, the irritable bowel syndrome is characterized by diarrhea without abdominal pain or constipation. In some embodiments, the irritable bowel syndrome satisfies the Rome II criteria. In some embodiments, the irritable bowel syndrome satisfies the Rome III criteria.

In some embodiments, the irritable bowel syndrome includes constipation (IBS-C). In some embodiments, the constipation is defined as hard or lumpy stools (e.g., Bristol Stool Form Scale 1-2) for greater than or equal to 25% of bowel movements with less than 25% of bowel movements having loose or water stools (e.g., Bristol Stool Form Scale 6-7). In other embodiments, the irritable bowel syndrome includes diarrhea (IBS-D). In some embodiments, the diarrhea is defined as loose or watery stools (e.g., Bristol Stool Form Scale 6-7) for greater than or equal to 25% of bowel movements with less than 25% of bowel movements having hard or lumpy stools (e.g., Bristol Stool Form Scale 1-2). In other embodiments, the irritable bowel syndrome includes both constipation and diarrhea (IBS-M). In some such embodiments, diarrhea defined by loose or watery stools (e.g., Bristol Stool Form Scale 6-7) is present for greater than or equal to 25% of bowel movements and constipation defined by hard or lumpy stools (e.g., Bristol Stool Form Scale 1-2) is present for greater than or equal to 25% of bowel movements. In still other embodiments, the irritable bowel syndrome includes no consistent abnormality of stool consistency (unsubtyped IBS).

In some embodiments, the adsorbent carbon microspheres act to reduce abdominal discomfort or pain associated with IBS. In some embodiments, the adsorbent carbon microspheres act to reduce gas associated with IBS. In some embodiments, the reduction in gas causes a reduction in abdominal distention, belching, and/or flatulence.

Production of Adsorbent Carbon Microspheres

Adsorbent carbon microspheres suitable for use as described herein may be produced by any suitable method, including but not limited to the following:

First, a dicyclic or tricyclic aromatic compound or a mixture thereof having a boiling point of 200° C. or more is added as an additive to a pitch such as a petroleum pitch or a coal pitch. The whole is heated and mixed, and then shaped to obtain a shaped pitch. Thereafter, the shaped pitch is dispersed and granulated in hot water at 70 to 180° C., with stirring, to obtain a microspherical shaped pitch. The aromatic additive is extracted and removed from the shaped pitch by a solvent having a low solubility to the pitch but a high solubility to the additive. The resulting porous pitch is oxidized by an oxidizing agent to obtain a porous pitch subject to heat infusibility. The resulting infusible porous pitch is treated at 800 to 1000° C. in a gas flow such as steam or carbon dioxide gas reactive with carbon to obtain a porous carbonaceous substance.

The resulting porous carbonaceous substance is then oxidized in a temperature range of 300 to 800° C., preferably 320 to 600° C., in an atmosphere containing 0.1 to 50% by volume, preferably 1 to 30% by volume, particularly preferably 3 to 20% by volume, of oxygen. The substance is thereafter reduced in a temperature range of 800 to 1200° C., preferably 800 to 1000° C., in an atmosphere of a non-oxidizable gas to obtain the final product. More details of suitable production processes and suitable products may be found in U.S. Pat. Nos. 4,681,764 and 6,830,753 and U.S. Application Publication No. 2005/0112114, filed May 26, 2005, all of which are incorporated herein by reference in their entirety. Suitable adsorbent carbon microspheres are commercially available from Kureha Corp., and is sold in Japan under the trade name KREMEZIN® (also known as AST-120).

Administration

For use as described herein, adsorbent carbon microspheres may be administered to the gut of a subject by any suitable means. In one embodiment, the carbon is administered orally. Formulations for oral administration may include, but are not limited to, free flowing microspheres, granules, tablets, sugar-coated tablets, capsules, suspensions, sticks, divided packages, or emulsions. In the case of capsules, gelatin capsules, or if necessary, enteric capsules may be used. In the case of tablets, the formulations may advantageously be adapted to break into the original fine particles inside the body. The adsorbent may be used as a mixture with an electrolyte-controlling agent, such as an aluminum gel or KAYEXALATE® (Windrop Lab, U.S.A.) or other agents.

The oral dosage administered to a subject may be any amount suitable to achieve the desired therapeutic result. In some embodiments, the oral dosage in the case of a human is about 1 to 20 g of the adsorbent per day. In some embodiments, the daily dosage may be divided into multiple administrations (e.g. into two to four portions daily). In some embodiments each unit dose is from about 1 g to about 5 g (e.g., about 2 g to about 3 g). In some embodiments, dosages of the adsorbent are individually packaged so as to preserve the adsorptivity of the material. For example, divided packaging may be used such as described in more detail in U.S. Pat. No. 5,686,081, which is incorporated herein by reference in its entirety. The divided packaging may contain unit doses of the adsorbent carbon microspheres in their free flowing form. The microspheres may be ingested with the aid of a liquid or soft food (e.g., apple sauce).

EXAMPLES

Example 1

Reduction of NO Levels in Murine Models

A model of chronic colitis was induced in BALB/c mice by administration of 5% dextran sulfate sodium (DSS) in sterile drinking water for 7 days. Although DSS-induced colitis murine models are primarily used to study inflammatory bowel disease, these models exhibit elevated levels of nitric oxide, which has also been associated with irritable bowel syndrome. See e.g. Yazar A., et al., "The urinary 5-hydroxyindole acetic acid and plasma nitric oxide levels in irritable bowel syndrome: a preliminary study," *Scottish Medical Journal,* 50(1):27-29. Fifteen mice with the DSS-induced colitis were administered 4 g/kg body weight of KREMEZIN® obtained from Kureha Corp mixed in their food. Five mice that received neither DSS nor KREMEZIN® were used as a control. In addition, for comparison purposes, five mice received only KREMEZIN® and fifteen mice received only DSS. The serum nitric oxide levels of all mice were measured.

FIG. 1 is bar graph depicting the average serum nitric oxide levels for each group of mice. As demonstrated by the graph, the mice with DSS-induced colitis that did not receive KREMEZIN® exhibited significantly elevated serum nitric oxide levels. In contrast, mice with DSS-induced colitis also receiving KREMEZIN® had significantly reduced serum levels of nitric oxide. These results suggest that adsorbent carbon microspheres such as KREMEZIN® are useful for the treatment of irritable bowel syndrome.

Example 2

Double-blind Clinical Study of Diarrhea-predominant Irritable Bowel Syndrome (IBS-D)

A phase 2, randomized, multicenter, placebo-controlled study with an eight week double blind treatment course followed by eight weeks of single-blind active treatment is conducted. The adsorbent carbon microspheres used in the study is KREMEZIN® obtained from Kureha Corp. packaged in 2 g sachets. The placebo is CELPHERE® CP-350 (Asahi Kasei Kogyo Kabushiki Kaisha Corp., Japan) stained to match the appearance of KREMEZIN®.

Approximately 100 patients diagnosed with IBS-D are randomized to either a KREMEZIN® or placebo group. Diagnosis is based on the Rome III criteria. The adsorbent carbon microspheres or cellulose placebo are administered in 2 g doses three times daily. Administration occurs approximately 30 minutes after a meal for eight complete weeks followed by a two week screening period.

The percent of patients who achieve at least a 50% reduction in the number of days with abdominal pain at the end of the first eight week treatment course is determined. The results indicate that a greater percentage of patients receiving KREMEZIN® experience the reduction as compared to patients receiving the cellulose placebo.

The percentage change in the IBS-QUOL score, Bristol Scale score, pain score, and individual items in an IBS symptom questionnaire are also determined for each patient. The results indicate on average a greater efficacious change in one or more of these scores for patients receiving KREMEZIN® as compared to those receiving the cellulose placebo.

Example 3

A human patient suffering from irritable bowel syndrome characterized by abdominal discomfort or pain and one or both of constipation and diarrhea is administered adsorbent carbon microspheres having particle sizes between about 0.05 and about 2 mm. Two grams of the adsorbent carbon microspheres are administered orally three times daily. The symptoms of the irritable bowel syndrome are reduced after repeated administration of the spherical carbon.

Example 4

A human patient suffering from irritable bowel syndrome and experiencing symptoms of abdominal distention, increased belching, or increased flatulence is administered adsorbent carbon microspheres having particle sizes between about 0.05 and about 2 mm. Two grams of the adsorbent carbon microspheres re administered orally three times daily. The amount of gas in the intestines of the patient is reduced after repeated administration of the spherical carbon.

Example 5

A human patient suffering from irritable bowel syndrome characterized by abdominal discomfort or pain and one or both of constipation and diarrhea is administered adsorbent carbon microspheres having particle sizes between about 0.05 and about 2 mm. Two grams of the adsorbent carbon microspheres is administered orally three times daily. The abdominal discomfort or pain is reduced after repeated administration of the spherical carbon.

Although the invention has been described with reference to embodiments and examples, it should be understood that numerous and various modifications can be made without departing from the spirit of the invention. Accordingly, the invention is limited only by the following claims.

What is claimed is:

1. A method of treating one or more symptoms of irritable bowel syndrome, comprising:
   identifying a subject suffering from irritable bowel syndrome; and
   administering to the subject adsorbent carbon microspheres having a particle size of about 0.01 to about 2 mm.

2. The method of claim 1, wherein the irritable bowel syndrome is characterized by abdominal discomfort or pain and one or both of constipation and diarrhea.

3. The method of claim 1, wherein the irritable bowel syndrome is characterized by abdominal discomfort or pain that has at least two characteristics selected from the group consisting of: 1) the discomfort or pain is relieved or improved by defecation, 2) onset of the discomfort or pain is associated with changes in stool frequency, and 3) onset of the discomfort or pain is associated with changes in stool form.

4. The method of claim 1, wherein the irritable bowel syndrome is characterized by diarrhea without abdominal pain or constipation.

5. The method of claim 1, wherein the irritable bowel syndrome comprises loose or watery stools in at least 25% or greater of bowel movements.

6. The method of claim 1, wherein the irritable bowel syndrome satisfies Rome II criteria.

7. The method of claim 1, wherein the irritable bowel syndrome satisfies Rome III criteria.

8. The method of claim 1, wherein an amount of the adsorbent carbon microspheres sufficient to achieve at least a 50% reduction in the number of days the subject experiences abdominal pain is administered.

9. The method of claim 1, wherein about 2 g of adsorbent carbon microspheres are administered three times daily.

10. A method of treating irritable bowel syndrome, comprising:
    identifying a subject suffering from abdominal discomfort or pain associated with irritable bowel syndrome; and
    administering to the subject an amount of adsorbent carbon microspheres having a particle size of about 0.01 to about 2 mm sufficient to reduce the abdominal discomfort or pain.

11. The method of claim 10, wherein the amount of the adsorbent carbon microspheres is sufficient to achieve at least a 50% reduction in the number of days the subject experiences abdominal pain or discomfort.

12. A method of treating irritable bowel syndrome, comprising:
   identifying a subject suffering from abdominal distention, increased belching, or flatulence associated with irritable bowel syndrome; and
   administering to the subject an amount of adsorbent carbon microspheres having a particle size of about 0.01 to about 2 mm sufficient to reduce gas in the subject.

13. The method of claim 1, 10, or 12, wherein the adsorbent carbon microspheres have a particle size of about 0.02 to about 1 mm.

14. The method of claim 1, 10, or 12, wherein the adsorbent carbon microspheres have a particle size of about 0.05 to about 0.8 mm.

15. The method of claim 1, 10, or 12, wherein the adsorbent carbon microspheres have a specific surface area of about 700 $m^2/g$ or more.

16. The method of claim 1, 10, or 12, wherein the adsorbent carbon microspheres have a specific surface area of about 700 $m^2/g$ to about 2500 $m^2/g$.

17. The method of claim 1, 10, or 12, wherein the volume of pores in the adsorbent carbon microspheres having a pore diameter of about 20 to about 15,000 nm is from about 0.04 mL/g to about 0.10 mL/g.

18. The method of claim 1, 10, or 12, wherein the total amount of acidic groups in the adsorbent carbon microspheres is about 0.30 to about 1.20 meq/g.

19. The method of claim 1, 10, or 12, wherein the total amount of basic groups in the adsorbent carbon microspheres is about 0.20 to about 1.00 meq/g.

* * * * *